United States Patent [19]

Nardi et al.

[11] Patent Number: 4,550,115
[45] Date of Patent: Oct. 29, 1985

[54] CERTAIN PIPERIDINO-LOWER-ALKYLENE ESTERS OF 3-METHYLFLAVONE-8-CARBOXYLATES POSSESSING SMOOTH MUSCLE RELAXANT ACTIVITY

[75] Inventors: Dante Nardi; Alberto Tajana; Renzo Pennini, all of Milan; Pietro Cazzulani, Casal Pusterlengo; Gabriele Graziani, Arese; Silvano Casadio, Milan, all of Italy

[73] Assignee: Recordati S.A., Chemical & Pharmaceutical Company, Chiasso, Switzerland

[21] Appl. No.: 397,196

[22] Filed: Jul. 12, 1982

[30] Foreign Application Priority Data

Jul. 17, 1981 [GB] United Kingdom ............... 8122158

[51] Int. Cl.[4] ................ C07D 311/30; A61K 31/445
[52] U.S. Cl. .................... 514/320; 546/196; 546/126; 546/133; 514/304; 514/305
[58] Field of Search ............ 546/196; 424/267; 514/320

[56] References Cited

U.S. PATENT DOCUMENTS 2,921,070  1/1960  daRe .................... 544/151

OTHER PUBLICATIONS

The Merck Index, Ninth Edition, p. 533, (1976).
Nomura et al., Chem. Abstracts, vol. 88, No. 19, Abst. No. 130, 978c, May 8, 1978.
A. Cova, et al., "Flavoxate and 3-Methylflavone-8-carboxylic Acid", *Arzneim.-Forsch.,* (Drug Res.), vol. 25, No. 11, pp. 1707–1709, (1975).
T. Argia, et al., "Gaschromatographic Determination of Flavoxate and Its Metabolites in Plasma and Urine After Oral Administration to Healthy Volunteers," *Ann. Sankyo Res. Lab,* vol. 26, pp. 94–105, (1974).
M. Windholz, et al., "#4012 Flavoxate," *The Merck Index,* p. 533, Merck & Co., Inc., Rahway, N.J., (1976).
A. Nomura et al., "General Pharmocological Studies on Flavoxate Hydrochloride (2-piperidinoethyl-3-methylflavone-8-carboxylate hydrochloride)", *Oyo Yakuri,* vol. 10, #3, pp. 365–381, (1975); see *Chem. Abst.,* vol. 88, 103978c, (1978).
C. S. Weil, "Table for Convenient Calculation of Median Effective Dose ($LD_{50}$ or $ED_{50}$) and Instructions in Their Use," *Biometrics,* vol. 8, p. 249ff, (1952).
M. Ferrari and F. Carpenedo, "On the Mechanism of Action of Some Myolytic Agents on Depolarized Guinea Pig Taenia Coli," *Arch. Int. Pharmocodyn. (France),* vol. 174, pp. 223–232, (1968).

*Primary Examiner*—Alan L. Rotman
*Attorney, Agent, or Firm*—Burns, Doane, Swecker & Mathis

[57] ABSTRACT

Novel 3-methylflavone-8-carboxylates having the structural formula (I):

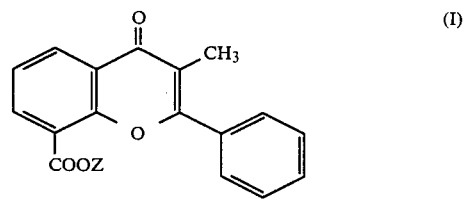

wherein Z is N-methylpiperidinyl, tropinyl or quinuclidinyl, or a group having the structural formula (II):

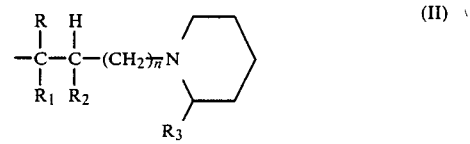

in which n is 0 or 1, R is hydrogen or alkyl having from 1 to 4 carbon atoms, or phenyl, $R_1$ is hydrogen or alkyl having from 1 to 4 carbon atoms, $R_2$ is hydrogen or hydroxy, and further wherein R, $R_1$ and $R_2$ may together form, with the carbon atoms from which they depend, a cycloalkyl ring having from 4 to 6 carbon atoms, and $R_3$ is hydrogen or alkyl having from 1 to 4 carbon atoms, with the proviso that R, $R_1$, $R_2$ and $R_3$ cannot at the same time all be hydrogen, and the pharmaceutically acceptable salts thereof, are effective smooth muscle relaxants, calcium blockers, anaesthetics and anti-inflammatories.

19 Claims, No Drawings

CERTAIN PIPERIDINO-LOWER-ALKYLENE ESTERS OF 3-METHYLFLAVONE-8-CARBOXYLATES POSSESSING SMOOTH MUSCLE RELAXANT ACTIVITY

BACKGROUND OF THE INVENTION

1. Field of the Invention

The present invention relates to certain novel esters of 3-methylflavone-8-carboxylic acid, to the pharmaceutically acceptable salts and process for the preparation thereof, and to various therapeutically effective pharmaceutical compositions comprising same.

2. Description of the Prior Art

It is known to this art that certain esters of 3-methylflavone-8-carboxylic acid exhibit a good spasmolytic activity. Compare U.S. Pat. No. 2,921,070, assigned to the assignee hereof. Nonetheless, such esters are not especially stable at physiological pH.

SUMMARY OF THE INVENTION

Accordingly, a major object of the present invention is the provision of certain novel esters of 3-methylflavone-8-carboxylic acid, such esters displaying marked stability at physiological pH, and such esters having the structural formula (I):

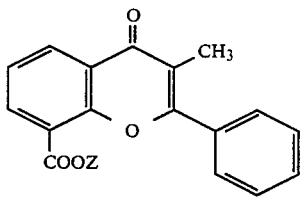

(I)

wherein Z is an N-methylpiperidinyl, tropinyl (preferably tropin-3-yl) or quinuclidinyl (preferably quinuclidin-3-yl) group or a group having the structural formula (II):

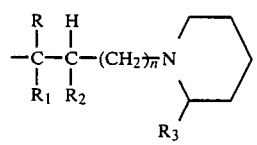

(II)

in which n is 0 or 1, R is a hydrogen atom, an alkyl group having from 1 to 4 carbon atoms or a phenyl group, $R_1$ is a hydrogen atom or an alkyl group having from 1 to 4 carbon atoms, $R_2$ is a hydrogen atom or a hydroxy group, and further wherein R, $R_1$ and $R_2$ may together form, with the carbon atoms from which they depend, a cycloalkyl ring having from 4 to 6 carbon atoms, and $R_3$ is a hydrogen atom or an alkyl group having from 1 to 4 carbon atoms, with the proviso that R, $R_1$, $R_2$ and $R_3$ cannot at the same time all be hydrogen, and the pharmaceutically acceptable salts of such esters.

DETAILED DESCRIPTION OF THE INVENTION

More particularly according to this invention, the subject novel esters have been found to exhibit powerful smooth muscle relaxant, calcium blocking, local anaesthetic, and anti-inflammatory properties. They are also markedly stable at physiological pH, such that the half-life of the drug is greatly prolonged. It too has been found, moreover, that the subject novel esters possess additional activities, whereas their toxicity is diminished or, at most, unaltered when compared with the known compounds.

This invention also features a process for the preparation of the compounds having the structural formula (I) as above defined, said process comprising condensing a 3-methylflavone-8-carboxylic acid halide having the structural formula (III):

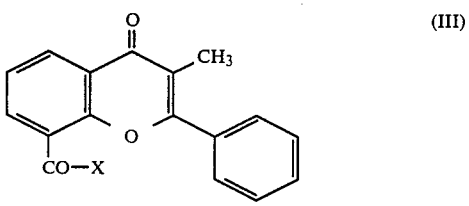

(III)

wherein X represents a halogen atom, with an aminoalcohol having the structural formula ZOH, wherein Z is as above defined.

The 3-methylflavone-8-carboxylic acid halide starting material is preferably 3-methylflavone-8-carboxylic acid chloride (III, X=Cl), and is a known compound (see U.S. Pat. No. 2,921,070). Same is readily prepared by reacting the corresponding acid with thionyl chloride, or with phosphorus trichloride. The acid is prepared according to the standard procedures for the preparation of flavones.

The condensation may be carried out either in the presence or absence of a solvent. If carried out in the absence of a solvent, the reactants are heated together at a temperature of from 140° C. to 200° C., and an excess of the 3-methyl-flavone-8-carboxylic acid is employed. If carried out in the presence of a solvent, the reactants are typically used in equimolar proportions, the temperature may range from 0° C. to the reflux temperature of the solvent, and an acid-binding agent (hydrogen halide acceptor) may optionally be present. Suitable solvents include all inert inorganic solvents, particularly dimethylformamide, ethers and halogenated hydrocarbons. Aromatic hydrocarbons, such as benzene and toluene, are also useful, especially when the reaction is carried out at reflux temperature. The acid-binding agent may be any of those customarily used in such condensations, for example, organic bases such as triethylamine and inorganic bases such as alkali metal hydroxides and alkali metal carbonates.

Another object of this invention is the provision of a process for the preparation of the compounds having the structural formula (I) in which Z represents a group of the structural formula (II) wherein n is 1, R and $R_1$ are both hydrogen atoms and $R_2$ is a hydroxy group. This additional process comprises reacting a compound having the structural formula (IV):

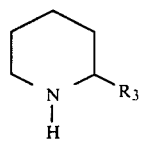

(IV)

wherein $R_3$ is as above defined, with 2,3-epoxypropyl-3-methylflavone-8-carboxylate in the presence of a catalyst. The 2,3-epoxypropyl 3-methylflavone-8-carboxylate is itself a novel compound, but is conveniently prepared by condensing a 3-methylflavone-8-carboxylic acid halide (preferably the chloride) with 2,3-epoxy-1-propanol. The reaction may be carried out in the presence of an organic solvent, such as any of those previously mentioned, or a nitrile such as acetonitrile. The catalyst may be an organic base, such as triethylamine.

Typically, equimolar amounts of reactants are employed, and the temperature of reaction ranges from 20° to 80° C. The reaction is preferably carried out at 40°–60° C.

The pharmaceutically acceptable salts according to the invention may be prepared from the free base esters obtained by the processes described above, in accordance with conventional methods well known to this art, such as addition of an acid to the free base dissolved in a suitable solvent. Suitable acids include hydrogen halides, phosphoric acid, nitric acid, alkylsulfonic acids, arylsulfonic acids, monofunctional and bifunctional carboxylic acids, hydroxycarboxylic acids and 1,5-naphthalenedisulfonic acid, and the like. Isolation and purification are also carried out conventionally.

The present invention also features pharmaceutical compositions comprising a compound having the structural formula (I) as above defined, or a pharmaceutically acceptable salt thereof, in admixture with conventional pharmaceutically acceptable diluent or carrier. Suitable such carriers will be apparent to those skilled in the art. Compare for example, *Remington's Pharmaceutical Sciences*, 4th Edition (1970).

The active compounds according to this invention exhibit a powerful smooth muscle relaxant and a calcium blocking action. They are also good anaesthetic and antiinflammatory agents. As stated above, their stability at physiological pH is, however, most dramatic when compared with related flavone derivatives. Such stability was measured at 37° C. in simulated gastric fluid (U.S. Pat. No. XX, 1105, 1980) and in phosphate buffer (pH 7.4) by spectrodensitometric determination of 3-methylflavone-8-carboxylic acid resulting from eventual hydrolysis. For purposes of comparison, 2-(N-piperidino)ethyl 3-methylflavone-8-carboxylate hydrochloride (Flavoxate) was selected, this compound being the best of the esters disclosed in U.S. Pat. No. 2,921,070, as well as being the compound most closely structurally related to the subject esters.

The results of such measurements are reported in Table I which follows. In this Table, and in the subsequent Tables, the numbers identifying the active compounds are those assigned to the respective active compounds in the Examples which follow and which describe their preparation.

TABLE I

| Active compound | Stability test, pH 7.4 | |
|---|---|---|
| | after 1 hour | after 3 hours |
| 1 | 100 | 100 |
| 2 | 100 | 100 |
| 3 | 40 | 30 |
| 4 | 68 | 34 |
| 5 | 96 | 91 |
| 6 | 100 | 100 |
| 7 | 44 | 25 |
| 8 | 85 | 70 |
| 9 | 88 | 87 |
| 10 | 100 | 100 |
| 11 | 100 | 100 |
| 12 | 100 | 100 |
| 13 | 100 | 100 |

TABLE I-continued

| Active compound | Stability test, pH 7.4 | |
|---|---|---|
| | after 1 hour | after 3 hours |
| FLAVOXATE | 22 | 10 |

The $LD_{50}$ of the subject novel esters was determined in mice, both i.p. and per os, following the method described by C. S. Weil [*Biometrics*, 8, 249 (1952)]. The results obtained are reported in the following Table II.

TABLE II

| Active compound | $LD_{50}$ mM/Kg | |
|---|---|---|
| | i.p. | os |
| 1 | 0.56 | 1.86 |
| 2 | 0.16 | 0.69 |
| 3 | 0.5 | 0.85 |
| 7 | 0.58 | 3.10 |
| 8 | — | 2.16 |
| 9 | 0.19 | 1.08 |
| 10 | 0.15 | 0.85 |
| 11 | 0.36 | 0.77 |
| 12 | 0.42 | 0.95 |
| 13 | 0.12 | 0.50 |
| FLAVOXATE | 0.90 | 1.89 |

The calcium blocking activity was tested on guinea pig depolarized taenia coli, according to the method described by Ferrari and Carpenedo [*Arch. Int. Pharmacodyn.*, 174, 223 (1968)]. The guinea pig taenia coli was allowed to stabilize in Tyrode solution without $Ca^{++}$. It was then washed with $K_2SO_4$ Ringer solution and afterwards perfused with $KNO_3$ Ringer. Cumulative concentrations of $CaCl_2$ were added to the organ bath in absence or presence of the test drug. The results obtained are reported in the following Table III.

TABLE III

| Calcium blocking activity | |
|---|---|
| Active compound | $ED_{50}$ ($\mu$M) |
| 1 | 24 |
| 2 | 16 |
| 3 | 19 |
| 5 | 8.6 |
| 6 | 7.5 |
| 8 | 7.3 |
| 9 | 26 |
| FLAVOXATE | 25 |

The antispastic or antispasmodic activity was evaluated following the Magnus method [*Pflugers Arch. Gen. Physiol.*, 102, 123 (1904)]. Two equal contractions were induced by $BaCl_2$ at a concentration ranging between 1 and $4.10^{-4}M$ in guinea pig ileum maintained at 30° C. in Ringer solution and aerated with Carbogen.

The test drug was administered and, one minute later, $BaCl_2$ in the same concentration. The inhibition of the contraction was observed. The results are reported in the following Table IV.

TABLE IV

| Active compound | $ED_{50}$ ($\mu$M) |
|---|---|
| 1 | 4 |
| 2 | 6.2 |
| 3 | 9.7 |
| 4 | 6.7 |
| 5 | 2.4 |
| 6 | 3.4 |
| 8 | 2.7 |
| 9 | 4 |
| 12 | 4.3 |

TABLE IV-continued

| Active compound | ED$_{50}$ (μM) |
| --- | --- |
| 13 | 2.1 |
| 14 | 7.7 |
| FLAVOXATE | 5.6 |

The smooth muscle relaxant activity of the novel flavone derivatives was also measured through the spontaneous mobility of guinea pig isolated ureter. The test was executed according to the Trendelemburg method [*Arch. Exp. Path. Pharmak.*, 81, 55 (1917)]. The ureter was allowed to stabilize in Tyrode solution with the upper part closed and the inner part connected to a pressure transducer. The test drugs were given cumulatively and the spontaneous circular and longitudinal contractions of the ureter were measured. The results obtained are reported in the following Table V.

TABLE V

Antispastic Activity Isolated Ureter (ED$_{50}$, μM)

| Active compound | circular contractions | longitudinal contractions |
| --- | --- | --- |
| 1 | 8.5 | 6.9 |
| 5 | 12 | 2.8 |
| 6 | 5.3 | 2.5 |
| 8 | 5 | 2.5 |
| 12 | 20 | 9 |

In order to further illustrate the present invention and the advantages thereof, the following specific examples are given, it being understood that same are intended only as illustrative, and in nowise limitative.

EXAMPLE 1

To a mixture consisting of 7.86 g of 3-(2-methyl-N-piperidino)-propanol, 40 ml of anhydrous dimethylformamide and 10.5 g of anhydrous potassium carbonate, 14.9 g of 3-methyl-flavone-8-carboxylic acid chloride were added. The mixture was heated at 60° C. for 8 hours under stirring, and was then poured into 500 ml of ice water. The precipitate thus formed was extracted with diethyl ether, washed with water and dried. The solvent was evaporated off and the compound, a brown oily residue, was transformed into the corresponding hydrochloride (1) by adding hydrogen chloride in isopropanol thereto. The 3-(2-methyl-N-piperidino)-propyl 3-methylflavone-8-carboxylate hydrochloride melted at 185°–187° C.

EXAMPLE 2

To a stirred suspension consisting of 5.75 g of 3-hydroxy-N-methylpiperidine and 10.4 g of anhydrous potassium carbonate in 50 ml dimethylformamide, 14.9 g of 3-methylflavone-8-carboxylate acid chloride were added. The mixture was stirred at ambient temperature for 20 hours, poured into ice water and the precipitate thus formed was extracted with ethyl acetate. The extract was neutralized with water and dried. The solvent was evaporated off and the residue was dissolved in isopropanol. After cooling, hydrogen chloride in isopropanol was added thereto. The hydrochloride (11) was washed with diethyl ether and crystallized from isopropanol. The desired N-methyl-3-piperidyl 3-methylflavone-8-carboxylate hydrochloride melted at 228°–229° C. The free base was crystallized from hexane, mp 90°–93° C.

EXAMPLE 3

To a stirred mixture, cooled to 10°–15° C., and consisting of 12.8 g of 3-hydroxyquinuclidine, 240 ml of dimethylformamide and 20 g of triethylamine, were added over 30–40 minutes 29.8 g of 3-methylflavone-8-carboxylic acid chloride. The temperature was allowed to reach 20°–25° C., the mixture was stirred for 4 hours and then poured into ice water. The precipitate thus formed was separated, washed with water and then extracted with ethyl acetate. The extract was washed with aqueous sodium carbonate solution, then with water and dried. The residue was chromatographed on a silica gel column using ethyl acetate:methanol (7:3 by volume) and chloroform:methanol (87:13 by volume) as eluent. 11.25 g of the desired compound, mp 180°–181° C., were obtained. The free base was transformed into the corresponding hydrochloride (13) by adding hydrogen chloride in ethanol thereto. The 3-quinuclidyl 3-methylflavone-8-carboxylate hydrochloride was crystallized from ethanol, mp 302°–205° C.

EXAMPLE 4

To a solution of 4.6 g of cis-2-piperidinocyclohexanol in 100 ml of anhydrous benzene, stirred and maintained at 20°–25° C., 7.5 g of 3-methylflavone-8-carboxylic acid chloride were added over a period of 15 minutes. The mixture was refluxed for 18 hours, then cooled to ambient temperature. The product thus formed was filtered off, washed with ethyl acetate, dried, and crystallized from ethanol. The cis-2-piperidino-cyclohexyl 3-methyl-flavone-8-carboxylate hydrochloride (8) melted at 258°–259° C. The trans form (14) was similarly obtained by starting from trans-2-piperidino-cyclohexanol. Its hydrochloride melted at 222°–225° C. Employing 1,1-dimethyl-(N-piperidino)ethanol instead of cis-2-piperidinocyclohexanol, 1,1-dimethyl-2-(N-piperidino)ethyl-3-methylflavone-8-carboxylate was prepared. The compound was isolated as its hydrochloride (5) of melting point 203°–207° C.

From this salt the free base was separated. It melted at 103°–105° C. Moreover, the following salts were also prepared:
 (i) Nitrate: mp. 179° C. (with decomposition)
 (ii) Sulfate: mp. 208° C. (with decomposition)
 (iii) Phosphate: mp. 175°–176° C. (with decomposition)
 (iv) Maleate: mp. 144°–148° C.
 (v) p-Toluenesulfonate: mp. 149°–152° C.

Employing 1,1-dimethyl-2-(2-methyl-N-piperidino)ethanol instead of cis-2-piperidinocyclohexanol, 1,1-dimethyl-2-(2-methyl-N-piperidinoethyl 3-methylflavone-8-carboxylate (6) was obtained. This compound, as hydrochloride, melted at 194°–195° C.

The free base was separated from this salt, and had a melting point of 78°–80° C. The following salts were also prepared:
 (i) Hydrobromide: mp. 209° C.
 (ii) Nitrate: mp. 170° C. (with decomposition)
 (iii) Sulfate: mp. 184°–188° C.
 (iv) Maleate: mp. 147°–149° C.
 (v) p-Toluenesulfonate: mp. 157°–159° C.

EXAMPLE 5

A mixture comprising 8.9 g of tropine hydrochloride and 22.5 g of 3-methylflavone-8-carboxylic acid chloride was heated for 4 hours at 170°–175° C. under a nitrogen atmosphere. When the reaction was complete, an additional 7.5 g of the flavone derivative were added and the mixture was heated again for 11 hours at the same temperature. After cooling, the product was powdered, suspended in water and stirred for 6 hours. The entire reaction mass was filtered off and dilute sodium hydroxide solution was added to the solution. The precipitate was centrifuged, washed with water and dried. The desired compound, 3-tropinyl-3-methylflavone-8-carboxylate, was treated with hydrogen chloride in ethanol to provide the corresponding hydrochloride (12), melting point 276°–278° C.

EXAMPLE 6

21.3 g of 3-methylflavone-8-carboxylic acid were slowly added, over a period of 4 hours at 20° C., to a stirred solution of 5.55 g of 2,3-epoxy-1-propanol and 8.34 g of triethylamine in 165 ml of anhydrous benzene. The mixture was permitted to stand at 20°–25° C. for 20 hours, and then 60 ml of water were added. The entire reaction mass was stirred for 15 minutes and the layers were separated. The organic layer was washed and dried, the solvent was evaporated off and 18.95 g of 2,3-epoxypropyl 3-methylflavone-8-carboxylate, m.p. 103°–105° C., were obtained.

A mixture comprising 16.8 g of the 2,3-epoxypropyl 3-methylflavone-8-carboxylate, 100 ml of acetonitrile, 5.5 ml of piperidine and 7 ml of triethylamine was heated at 60° C. for 12 hours. The solvent was evaporated off and the brown, oily residue was washed twice with 75 ml of benzene. The 2-hydroxy-3-(N-piperidino)-propyl 3-methylflavone-8-carboxylate thus formed was converted into the corresponding hydrochloride (7) in the usual manner. Mp 187°–189° C.

EXAMPLE 7

Following the procedure described in Example 2, the following esters of 3-methylflavone-8-carboxylic acid were prepared from corresponding starting materials:
(2) 1-methyl-3-(N-piperidino)propyl, separated as its hydrochloride hemihydrate, mp 161°–168° C.;
(10) 1-methyl-4-piperidinyl, melting at 103°–105° C.;
(3) 1-methyl-piperidino-ethyl, separated as its hydrochloride hydrate, mp 218°–220° C.;
(4) 1-phenyl-2-piperidino-ethyl(hydrochloride) of melting point 219°–221° C.; and
(9) 2-piperidinomethyl cyclohexyl, as hydrochloride, mp 236°–237° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims:

What is claimed is:
1. A 3-methylflavone-8-carboxylic acid ester having the structural formula (I):

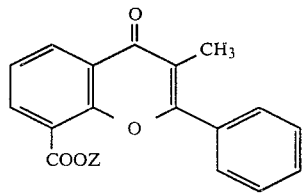

wherein Z is N-methylpiperidinyl or a group having the structural formula (II):

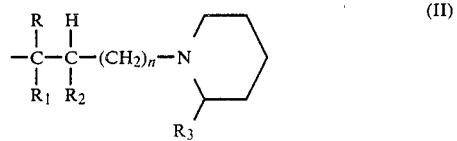

in which n is 0 or 1 R is hydrogen or alkyl having from 1 to 4 carbon atoms, $R_1$ is hydrogen or alkyl having from 1 to 4 carbon atoms, $R_2$ is hydrogen or hydroxy, and $R_3$ is hydrogen or alkyl having from 1 to 4 carbon atoms, with the proviso that R, $R_1$, $R_2$ and $R_3$ cannot at the same time all be hydrogen; and the pharmaceutically acceptable salts thereof.

2. The carboxylic acid ester as defined by claim 1, wherein Z in N-methylpiperidinyl.

3. The carboxylic acid ester as defined by claim 1, wherein Z has the structural formula (II).

4. The carboxylic acid ester as defined by claim 3, in which $R_3$ is alkyl.

5. The carboxylic acid ester as defined by claim 3, in which $R_2$ is hydroxy.

6. The carboxylic acid ester as defined by claim 3, in which at least one of R and $R_1$ is alkyl.

7. The carboxylic acid ester as defined by claim 3, in which both R and $R_1$ are alkyl.

8. The carboxylic acid ester as defined by claim 3, in which R, $R_1$ and $R_3$ are each alkyl.

9. The carboxylic acid ester as defined by claim 1, the same being 3-(2-methyl-N-piperidino)-propyl 3-methylflavone-8-carboxylate.

10. The carboxylic acid ester as defined by claim 1, the same being N-methylpiperidin-3-yl 3-methylflavone-8-carboxylate.

11. The carboxylic acid ester as defined by claim 1, the same being 1,1-dimethyl-2-(N-piperidino)-ethyl 3-methylflavone-8-carboxylate.

12. The carboxylic acid ester as defined by claim 1, the same being 2-hydroxy-3-(N-piperidino)-propyl 3-methylflavone-8-carboxylate.

13. The carboxylic acid ester as defined by claim 1, the same being 1-methyl-3-(N-piperidino)-propyl 3-methylflavone-8-carboxylate.

14. The carboxylic acid ester as defined by claim 1, the same being 1-methylpiperidin-4-yl 3-methylflavone-8-carboxylate.

15. The carboxylic acid ester as defined by claim 1, the same being 1-methyl-2-(N-piperidino)-ethyl 3-methylflavone-8-carboxylate.

16. The carboxylic acid ester as defined by claim 1, the same being 1-phenyl-2-(N-piperidino)-ethyl 3-methylflavone-8-carboxylate.

17. A composition of matter comprising a smooth muscle relaxant effective amount of the 3-methylflavone-8-carboxylate as defined by claim 1, or pharmaceutically acceptable salt thereof, and a pharmaceutically acceptable carrier therefor.

18. The method for eliciting a smooth muscle relaxant response in a warm-blooded mammal, comprising administering to a warm-blooded mammal in need of such treatment, a therapeutically effective amount of the 3-methylflavone-8-carboxylate as defined by claim 1, or pharmaceutically acceptable salt thereof.

19. The method for eliciting a smooth muscle relaxant response in a warm-blooded mammal, comprising administering to a warm-blooded mammal in need of such treatment, a therapeutically effective amount of the composition of matter as defined by claim 17.

* * * * *